United States Patent
Eppstein

(10) Patent No.: US 6,173,202 B1
(45) Date of Patent: Jan. 9, 2001

(54) METHOD AND APPARATUS FOR ENHANCING FLUX RATES OF A FLUID IN A MICROPORATED BIOLOGICAL TISSUE

(75) Inventor: Jonathan A. Eppstein, Atlanta, GA (US)

(73) Assignees: SpectRx, Inc., Norcross; Altea Technologies, Inc., Atlanta, both of GA (US)

(*) Notice: Under 35 U.S.C. 154(b), the term of this patent shall be extended for 0 days.

(21) Appl. No.: 09/036,053

(22) Filed: Mar. 6, 1998

(51) Int. Cl.[7] ..................................................... A61N 1/30
(52) U.S. Cl. ................................ 604/20; 604/22; 600/573
(58) Field of Search .......................... 604/20–22, 27–28, 604/520, 501, 502, 506; 600/573; 435/285.2, 173.6; 514/947

(56) References Cited

U.S. PATENT DOCUMENTS

| | | |
|---|---|---|
| 3,964,482 | 6/1976 | Gerstel et al. |
| 4,775,361 | 10/1988 | Jacques et al. |
| 5,016,615 | 5/1991 | Driller et al. |
| 5,115,805 | 5/1992 | Bommannan et al. |
| 5,215,520 | 6/1993 | Shroot et al. |
| 5,231,975 | 8/1993 | Bommanan et al. |
| 5,246,437 | 9/1993 | Abela. |
| 5,250,023 | 10/1993 | Lee et al. |
| 5,323,769 | 6/1994 | Bommannan et al. |
| 5,328,453 * | 7/1994 | Sibalis. |
| 5,427,585 * | 6/1995 | Bettinger. |
| 5,445,611 | 8/1995 | Eppstein et al. |
| 5,458,140 | 10/1995 | Eppstein et al. |
| 5,885,211 | 3/1999 | Eppstein et al. |
| 5,947,921 * | 9/1999 | Johnson et al. |
| B1 5,019,034 | 5/1995 | Weaver et al. |

FOREIGN PATENT DOCUMENTS

| | | |
|---|---|---|
| 2153223 | 6/1987 | (GB). |
| WO 94 09713 | 5/1994 | (WO). |
| WO 97/04832 | 2/1997 | (WO). |
| WO 97/07734 | 3/1997 | (WO). |
| WO 98/00193 | 1/1998 | (WO). |
| WO 98/29134 | 7/1998 | (WO). |

OTHER PUBLICATIONS

PCT International Search Report dated Oct. 28, 1999, No. PCT/US 99/04798.

Substance P Antagonist Does Not Block the Stimulation of Rapidly Adapting Pulmonary Stretch Receptors by Ammonia, S. Matsumoto et al., full citation unavailable.

Transdermal enhancer patent literature, G.C. Santus et al., *Journal of Controlled Release*, pp. 1–20, 1993.

Effects of Atmospheric Ammonia on Pulmonary Hemodynamics and Vascular Permeability in Pigs: Interaction with Endotoxins, Gustin et al., *Toxicology and Applied Pharmacology*, pp. 17–26, 1994.

Effects of ammonia and histomine on lung irritant receptors in the rabbit, Matsumoto, *Respiration Physiology*, pp. 301–308, 1989.

Effectiveness of Ammonium Solutionin relieving Type I Mosquito Bite Symptoms: A Double–Blind, Placebo–Controlled Study, Zhai et al., full citation unavailable.

Ammonia Amplifies Nicotine, Study Confirms, John Schwartz, *The Washington Post*, p. A04m Jul. 30, 1997.

Acute Pulmonary Edema, full citation unavailable.

(List continued on next page.)

Primary Examiner—Mark Bockelman
(74) Attorney, Agent, or Firm—Needle & Rosenberg, P.C.

(57) ABSTRACT

A method and apparatus for enhancing the flux rate of a fluid through a biological membrane. The method includes the steps of porating a section of the tissue to form one or more micropores in the tissue, and applying a flux enhancer to the tissue through the one or more micropores. The resulting enhancement of fluid flux in the tissue enables more effective harvesting from the body of fluids, as well as more effective delivery of a drug.

40 Claims, 6 Drawing Sheets

OTHER PUBLICATIONS

Synergistic Effect of Bile Acid, Endotoxin, and Ammonia on Brain Edema, Tominaga et al., *Metabolic Brain Disease*, pp. 93–105, 1991.

Ammonia secretion in sweat, Brusilow et al., *American Journal of Physiology*, pp. 513–517, 1968.

Early Changes in the permeability of the Blood–Brain Barrier Produced by Toxins Association with liver Failure, McClung et al., *Pediatric Research*, pp. 227–231, 1190.

Potential toxins of acute liver failure and their effects on blood–brain barrier permeability, Zaki et al., 1983, full citation unavailable.

Changes in the permeability of the blood–brain barrier in acute hyperammonemia. Effect of dexamethasone., Ziylan et al., full citation unavailable.

AfterBite, Product Advertisement, 1997.

AfterBite, News Release, Littleton, NH, Aug. 1994.

* cited by examiner

METHOD AND APPARATUS FOR ENHANCING FLUX RATES OF A FLUID IN A MICROPORATED BIOLOGICAL TISSUE

BACKGROUND OF THE INVENTION

1. Field of the Invention

The invention relates generally to the monitoring of analytes in the body and the transdermal delivery of drugs to the body. More particularly, the invention relates to enhancing the rate of flux of a substance collected from or delivered to a biological tissue through the poration of the skin or other biological membrane and the application of a flux enhancer to the porated biological membrane.

2. Description of Related Art

The transfer of materials across biological membranes is necessary in the practice of a variety of medical and other procedures. For example, to minimize complications resulting from diabetes, diabetics must periodically monitor and control their blood glucose levels. Typically, blood glucose monitoring is achieved by taking a sample of blood or other body fluid, and measuring the glucose level present in the sample. Historically, the samples have been obtained by piercing the skin with a needle or lancet. It is also frequently necessary to deliver a drug through the skin or other biological membrane. Most frequently, drugs are delivered transdermally by injection with a needled syringe. Such invasive sampling and drug delivery methods entail a number of disadvantages, most notably, discomfort and potential infection.

In an effort to address the inherent disadvantages of invasive sampling and delivery methods, several minimally invasive and non-invasive sampling and delivery techniques have been developed. "Minimally invasive," as used herein, refers to techniques in which a biological membrane or tissue is invaded by forming small holes or micropores in the surface of a tissue or membrane, but do not substantially damage the underlying, non-surface portions of the tissue or membrane. As used herein, "non-invasive" refers to techniques not requiring the entry of a needle, catheter, or other invasive medical instrument into the body. It has previously been discovered that blood glucose levels can be determined from an analysis of interstitial fluid, the clear fluid occupying the spaces between cells in the body, samples of which can be obtained through the skin by previously known minimally invasive or non-invasive sampling techniques. Previously known minimally invasive or noninvasive methods of sampling interstitial fluid, however, have not been fully successful for blood glucose monitoring purposes. One challenge facing minimally invasive or non-invasive methods is the ability to acquire a large enough sample of interstitial fluid in a short time to enable accurate glucose measurement with low cost disposable assay techniques.

The skin presents the largest, most readily accessible biological membrane through which an analyte may be collected or a drug delivered. Mucosal and buccal membranes present feasible, but less accessible, sites for collection and delivery. Unfortunately, the skin and, to a somewhat lesser extent, the mucosal and buccal membranes, are highly resistant to the transfer of materials therethrough. The skin generally comprises two main parts: the epidermis and the dermis. The epidermis forms the outer portion of the skin, and itself comprises several distinct layers. The outermost layer of the epidermis, the stratum corneum, is composed of denucleated, keratinized, clear, dead cells, and is typically between 10–30 $\mu$m thick. The stratum corneum is chiefly responsible for the skin's barrier properties and, therefore, is the layer of skin forming the primary obstacle to the transdermal flux of analytes out of the body and of drugs or other foreign materials or organisms into the body.

There have been significant advancements made in the transdermal transport of substances across a biological membrane by creating micropores in the biological membrane. See, for example, co-pending U.S. application Ser. No. 08/776,863 filed Feb. 7, 1997, entitled "Microporation of Human Skin for Drug Delivery and Monitoring Applications", the entirety of which is incorporated herein by reference. Nevertheless, there is a need to improve upon these techniques and particularly increase the rate at which substances are transported through a biological membrane.

SUMMARY OF THE INVENTION

Briefly, one aspect of the present invention involves a method for enhancing the flux rate of a fluid through biological tissue. The method generally comprises the delivering an effective amount of a flux enhancer into the tissue through at least one micropore in the tissue. Depending on the specific application, the flux enhancer is delivered to the micropore through any of a number of mechanisms, examples of which are described below. The depth of poration and of application of the flux enhancer can also be adjusted to suit the desired application.

Another aspect of the present invention involves a method of harvesting an analyte from tissue beneath a biological membrane. The method preferably includes the steps of porating the biological membrane to form at least one micropore, delivering an effective amount of a flux enhancer to the tissue through the micropore, and collecting a quantity of the analyte through the micropore. Again, the mechanism for delivering the flux enhancer can vary to suit the application, as can the depth of poration and application of the flux enhancer. The application of a motive force, such as suction, pressure, electric field, sonic energy, or concentration gradient, can also be employed to further enhance the rate of analyte harvesting.

Yet another embodiment of the present invention provides a method of delivering a drug through a biological membrane. The method preferably comprises porating a site of the membrane to form at least one micropore, delivering an effective amount of a flux enhancer into the micropore, and introducing a drug through the at least one micropore. Again, the mechanism for delivering the flux enhancer can vary to suit the application, as can the depth of poration and application of the flux enhancer. The application of a motive force, such as iontophoresis, pressure, electric field, sonic energy, or concentration gradient can also be employed to further enhance the rate of drug delivery into the tissue.

Still a further aspect of the present invention provides involves a device for facilitating the formation of micropores in a biological membrane and for enhancing the rate of flux of a fluid therethrough.

These and other features and advantages of the present invention will become apparent from the following description of the preferred embodiments, taken in conjunction with the drawings.

DETAILED DESCRIPTION OF THE PREFERRED EMBODIMENTS

Figure 1:
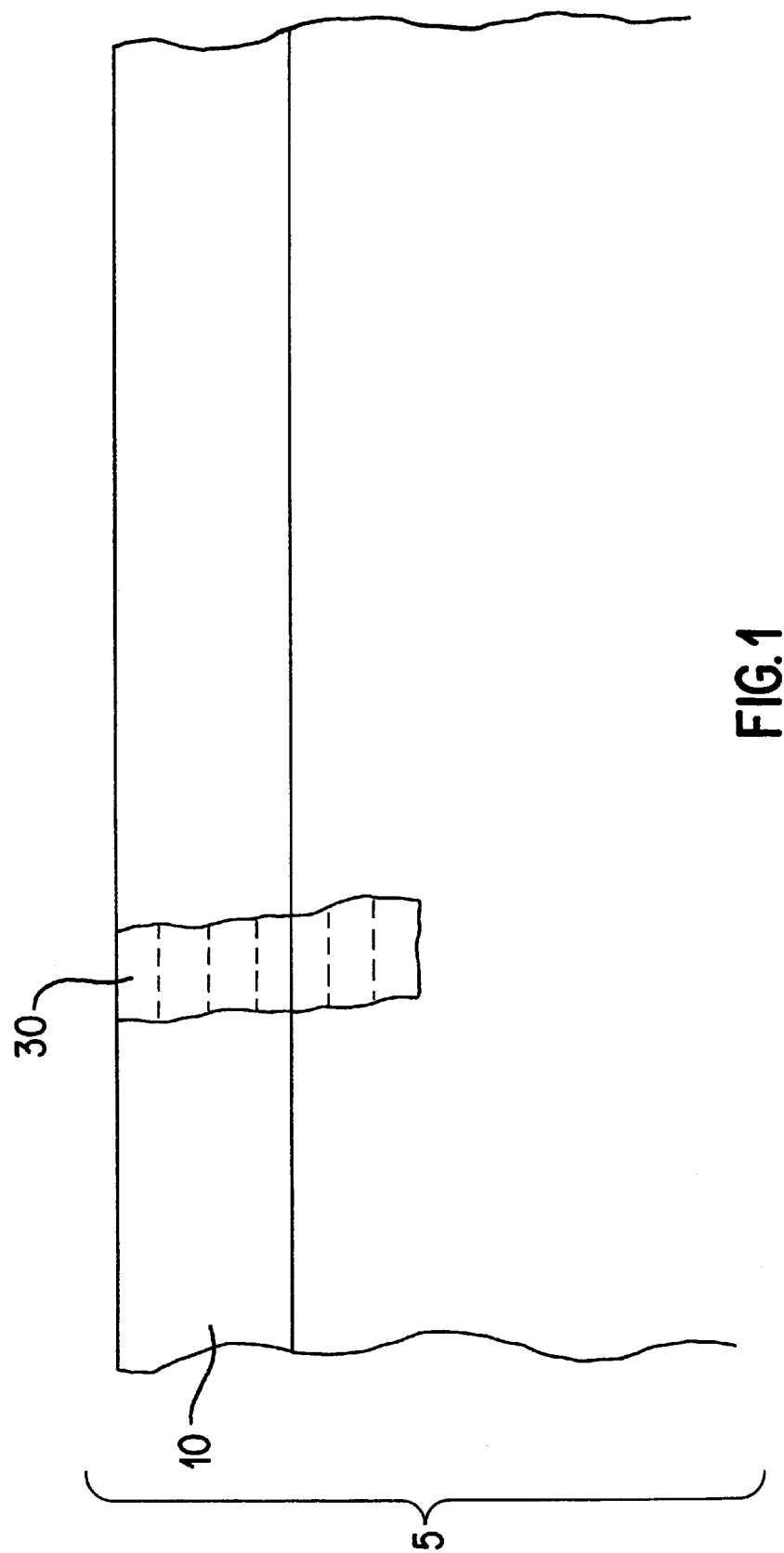
FIG. 1 is an enlarged cross-sectional view of a section of a biological membrane and underlying tissue porated according to one or more embodiments of the present invention.

The present invention will now be described in detail, by reference to several preferred embodiments. The embodiments described in detail herein are presented by way of example only, and are not intended to limit the scope of the invention defined in the claims, and equivalents thereof. Words and phrases used herein are intended to have their ordinary meanings, as understood by a person of ordinary skill in the art to which this invention pertains, unless otherwise defined.

Definitions

Unless the context clearly dictates otherwise, "a," "an," and "the" includes both singular and plural referents. Thus, for example, reference to delivery of "a drug" contemplates delivery of one or more drugs, reference to "a flux enhancer" contemplates one or more flux enhancers, and reference to "an analyte" contemplates one or more analytes. Also, unless the context clearly dictates otherwise, "in" means "in" or "on." As used herein, "including," "includes," or the like, means including, without limitation.

As used herein, "organism" or "individual" or "subject" or "body" refers to the entire human, animal, or plant being acted upon by the methods described herein.

As used herein, "biological tissue" or "tissue" means any component comprising some portion of an organism, including but not limited to: cells; intercellular substances surrounding cells; biological membranes; bone; collagen; fluids, including blood; epithelial tissue, including the skin; connective tissue; blood vessels; muscle tissue; nerve tissue; and the like.

As used herein, "biological membrane" or "membrane" means any tissue material present within a living organism forming a barrier between distinct tissues or areas of an organism, or between tissue of an organism and the external environment, and includes without limitation: the skin; mucosal membranes; buccal membranes; the outer layers of a plant; and the walls of a cell or a blood vessel.

As used herein, "skin" means the epidermis, which includes the stratum corneum, and the dermis.

As used herein, "mucous membrane" or "mucosa" refers to the epithelial linings of the mouth, nasopharynx, throat, respiratory tract, urogenital tract, anus, eye, gut and all other surfaces accessible via an endoscopic device such as the bladder, colon, lung, blood vessels, heart and the like.

As used herein, the "buccal membrane" includes the mucous membrane of the mouth.

As used herein, "into" or "in" a biological membrane or layer thereof includes penetration in or through only one or more layers (e.g., all or part of the stratum corneum or the entire outer layer of the skin or portion thereof).

As used herein, "through" a biological membrane or layer thereof means through the entire depth of the biological membrane or layer thereof As used herein, "transdermal" or "percutaneous" or "transmembrane" or "transmucosal" or "transbuccal" refers to passage of a substance into or through the subject biological membrane or tissue, in any direction.

As used herein, "poration," "microporation," or any such similar term means the formation of a small hole or pore to a desired depth in or through a biological membrane or tissue. The microporation process referred to herein is distinguished from electroporation principally by the minimum dimensions of the micropores formed. Micropores shall be no smaller than 1 micron across and at least 1 micron in depth, whereas the openings formed with electroporation are typically only a few nanometers in any dimension. Preferably the hole or micropore will be no larger than about 1 mm in diameter, and more preferably no larger than about 300 μm in diameter, and will extend to a selected depth, as described hereinafter.

As used herein, "micropore" or "pore" means an opening as described above, formed by the microporation method.

As used herein "ablation" means the controlled removal of material which may include cells or other components comprising some portion of a biological membrane or tissue caused by any of the following: kinetic energy released when some or all of the vaporizable components of such material have been heated to the point that vaporization occurs and the resulting rapid expansion of volume due to this phase change causes this material, and possibly some adjacent material, to be removed from the ablation site; thermal, mechanical, or sonic decomposition of some or all of the tissue at the poration site.

As used herein, "flux enhancer" means any material that increases the rate of flow of a fluid through a biological tissue or membrane by any mechanism. The fluid can be, for example: a bioactive agent, drug, analyte, dye, stain, microparticle, microsphere, compound, or some other chemical formulation. As described in greater detail below, the subject fluid flow can be, for example, the flow of interstitial fluid out of a porated biological tissue or membrane, or can be the flow of a drug into a porated biological tissue or membrane. Representative examples of mechanisms by which a flux enhancer can increase the rate of flow of a fluid through a tissue include, without limitation: the reduction of the fluid's viscosity; the dilation of intercellular pathways within the tissue; the reduction of the barrier properties of the capillary walls.

Materials that can be used as flux enhancers include, but are not limited to, ammonia related substances such as ammonia gas, ammonia heparin, and ammonia bicarbonate; vasodilators such as histamine, Platelet Activating Factor (PAF), bradykinin, nicotinic acid, and nitroglycerin; inflammatory mediators such as autacoids (histamine, bradykinin, eicanosoids such as prostaglandins, leukotrienes, and thromboxane), cytokines, and interleukins; neurotransmitters such as substance P, acetylcholine, and neurokinin A; growth factors such as Platelet-Derived Growth Factor (PDGF), and Vascular Endothelial Growth Factor (VEGF); mast cell degranulators such as substance P, and mastoparan; extracellular matrix adhesion inhibitors such as anti integrins, and disintegrins; enzymes such as hyaluronidase, trypsin, and papain; fungistatic compounds such as benzoic acid; compounds which release neuropeptides from nerve terminals such as capsaicin; keratolytic agents such as lactic acid, glycolic acid, and salicylic acid; blistering agents such as cantharidin; anticoagulants such as heparin and sodium fluoride; food oils such as mustard oil and peppermint oil; anti-pruritics such as camphor; diuretics such as ethacrynate sodium and furosemide; and capillary permeability enhancers (extravasants) such as VEGF, PAF, leukotrienes, kinins (bradykinin & kallidin), histamine, and estrogen. One material which has proven effective as a flux enhancer is an ammonia-based solution sold by Tender Corp., of Littleton, N.H. under the trademark AfterBite.

An "effective amount" of a flux enhancer is the quantity of material necessary to produce the desired increase of flow rate through the tissue.

As used herein, the term "bioactive agent," "drug," "pharmacologically active agent," or "deliverable substance" or any other similar term means any chemical or biological material or compound suitable for delivery by the methods previously known in the art and/or by the methods taught in the present invention, that induces a desired effect, such as a biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, (3) either alleviating, reducing, or completely eliminating the disease from the organism, and/or (4) placing within the viable tissue layers of the organism of a compound or formulation that can react, optionally in a reversible manner, to changes in the concentration of a particular analyte and in so doing cause a detectable shift in this compound or formulation's measurable response to the application of energy to this area. This energy may be electromagnetic, mechanical, or acoustic.

An "effective amount" of a drug means a sufficient amount thereof to effect a desired biological or pharmacological effect.

As used herein, "analyte" means any chemical or biological material or compound in an organism, suitable for sampling from a biological tissue or membrane by the technology taught in this present invention, or by technology previously known in the art, the presence, concentration, or other characteristics of which are sought to be determined. Glucose is a specific example of an analyte because it is a sugar suitable for passage through the skin, and individuals, for example those having diabetes, might want to know their blood glucose levels. Other examples of analytes include, but are not limited to, such compounds as sodium, potassium, bilirubin, urea, ammonia, calcium, lead, iron, lithium, salicylates, antibodies, hormones, or an exogenously delivered substance and the like.

Referring first to FIG. 1, the present invention is directed to a method for enhancing the rate of flux of a fluid collected from or delivered to a biological tissue 5 comprising a biological membrane 10. At certain depths in the biological membrane and in the sub-membrane tissue, there are cells and capillaries, and interstitial fluid suffuses the spaces between the cells and capillaries. For example, in skin there are capillaries in the dermis.

The biological tissue 5 is porated with one or more micropores 30 (typically several pores are formed at a site). The depth of a micropore can be selectively varied, according to the desired application. For example, FIG. 1 shows several possible depths of poration. The micropore 30 may extend into various depths of the biological membrane 10, or through the biological membrane 10 into sub-membrane tissue. For example, it may be desirable to porate to a sufficient depth into the biological membrane 5 to obtain more direct access to capillaries therein. An example is to porate into the dermis. The advantages of porating to selected depths is described in more detail hereinafter. Poration of the tissue 5, to form one or more micropores 30 of a selected depth therein, can be carried out by methods including ablation or micropuncture of the tissue 5 by a probe, hot wire or other heat source, an optical energy source, a sonic energy source, a microlancet, a high pressure fluid jet, or by some other energy source. Several exemplary embodiments of poration methods and devices for implementing the present invention are disclosed herein.

One such poration technique employs a heated probe, which is used to form one or more micropores of a selected depth in a biological tissue or membrane. The heated probe is useful in the embodiments shown in FIGS. 2 and 3. A heated probe can deliver sufficient energy into or through the hydrated viable tissue layers beneath the outer layer of the biological membrane so that the poration process can continue into the tissue to a selected depth, penetrating through deeper layers including, e.g., in the case of the skin, through the epidermis, the dermis, and into the subcutaneous layers below if desired. The principle concern of a system is designed to create a micropore extending some distance into or through the viable tissues beneath the stratum corneum, mucosal or buccal membranes is how to minimize both the damage to the adjacent tissue and the sensation to the subject during the poration process. Experimentally, it has been shown that a suitable heated probe is a solid, electrically or optically heated element, with the active heated probe tip physically defined to be no more than a few hundred microns across and protruding up to a few millimeters from the supporting base. A single pulse, or multiple pulses of current through the heated probe can deliver enough thermal energy into or through the tissue to allow the ablation to penetrate as deep as the physical design allows. The support base may act as a component to limit the extent of the penetration into the tissue, essentially restricting the depth to which the heated probe can penetrate into a micropore to contact fresh, unporated tissue. If the electrical and thermal properties of said heated probe, when it is in contact with the tissues, allow the energy pulse to modulate the temperature of the heated probe rapidly enough, this type of deep tissue poration can be accomplished with essentially no pain to the subject. Experiments have shown that if the required amount of thermal energy is delivered to the probe within less than roughly 20 milliseconds, than the procedure is painless. Conversely, if the energy pulse must be extended beyond roughly 20 milliseconds, the sensation to the subject increases rapidly and non-linearly as the pulse width is extended.

An electrically heated probe design that supports this type of selected depth poration can be built by bending a 50 to 150 micron diameter tungsten wire into a sharp kink, forming approximately an 180 degree bend with a minimal internal radius near the midpoint of the wire. This miniature 'V' shaped piece of wire can then be mounted such that the point of the 'V' extends some distance out from a support piece which has conductive electrodes deposited upon it. The distance to which the wire extends out from the support will define the maximum penetration distance into or through the tissue when the wire is heated. Each leg of the tungsten 'V' will be attached to one of the electrodes on the support carrier which in turn can be connected to the current pulsing circuit. When the current is delivered to the wire in an appropriately controlled fashion, the wire will rapidly heat up to the desired temperature to effect the thermal ablation process, either in a single pulse or in multiple pulses of current. By monitoring the dynamic impedance of the probe and knowing the relationship between the coefficient of resistance and the temperature of the tungsten element, closed loop control of the temperature of the heated element can easily be established. Also, by dynamically monitoring the impedance through the skin from the contact point of the probe (acting as an electrode) and a second electrode placed some distance away from the contact point of the probe, the depth of the pore can be controlled based on the different impedance properties of the tissue as a function of penetration depth.

An optically heated probe design that supports this type of selected depth poration can be built by taking an optical fiber and placing on one end a tip comprised of a solid cap or coating. A light source such as a laser diode is coupled into the other end of the fiber. The side of the tip closest to the fiber has a high enough absorption coefficient over the range of wavelengths, or selected wavelengths, emitted by the light source such that when the photons reach the end of the fiber and strike this absorbing material, some of them will be absorbed and subsequently cause the tip to heat up. The specific design of this tip, fiber, and source assembly may vary widely; however, fibers with gross diameters of 50 to 1000 microns across commercially available and sources emitting up to thousands of watts of optical energy are similarly commercially available. The tip forming the actual heat probe can be fabricated from a high melting point material, such as tungsten, and attached to the fiber by machining it to allow the insertion of the fiber into a cylindrical bore within the tip. If the distal end of the tip has been fabricated to limit the thermal diffusion away from this tip and back up the supporting cylinder attaching the tip to the fiber within the time frame of the optical pulse widths used, the photons incident upon this tip will elevate the temperature rapidly on both the fiber side and the contact side which is placed against the tissue surface. The positioning of the fiber/tip assembly onto the tissue surface can be accomplished with a simple mechanism designed to hold the tip against the tissue surface under some spring tension such that as the tissue beneath it is ablated allowing the tip to advance into the tissue. This allows the thermal ablation process to continue into or through the tissue as far as one desires. An additional feature of this optically heated probe design is that by monitoring the black body radiated energy from the heated tip that is collected by the fiber, a very simple closed loop control of the tip temperature can be effected. Also, as described earlier, by dynamically monitoring the impedance through the body from the contact point of the probe and a second electrode placed some distance away from the contact point of the probe, the depth of the pore can be determined based on the different impedance properties of the tissue as a function of the probe penetration into the tissue.

Impedance can be used to determine the depth of a pore made by any technique because it is well known that different tissue structures have different impedance characteristics. Accordingly, impedance can be used as an input to a control system for making pores of a selected depth. The impedance measured may be a complex impedance measured with a device (such as a network analyzer) that applies a signal with selected frequency components between two or more electrodes (one of which preferably being the heated probe) on or in the tissue to highlight the impedance properties of the selected tissues.

Delivery of the flux enhancer can be accomplished by a variety of methods and devices, several examples of which are more fully described herein. The delivery of the flux enhancer into the tissue can be carried out separately from the microporation of the biological membrane, or alternatively, microporation and delivery of the flux enhancer can be performed substantially simultaneously. If separately carried out, the flux enhancer may be delivered before or after microporation of the biological membrane.

Figure 2:
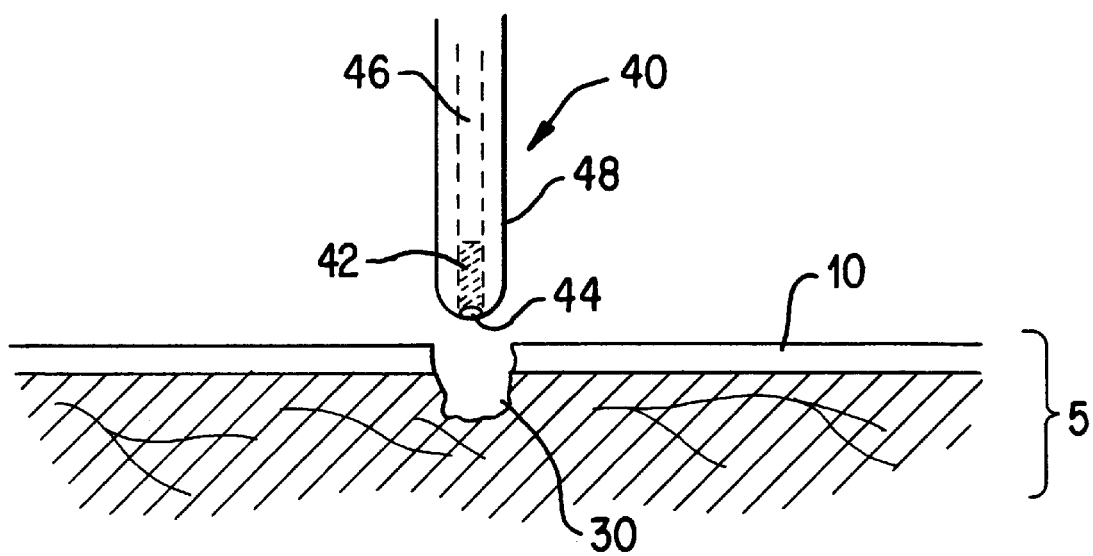
FIG. 2 is an enlarged diagram showing the use of a probe for delivery of a flux enhancer according to one embodiment of the present invention.

FIG. 2 shows the use of a probe or penetration device 40 for delivery of a quantity of flux enhancer 42 into biological tissue 5. The probe 40 can be provided with a sharp tip or edge 44, capable of penetrating or piercing the biological membrane 10 of the tissue 5, thereby allowing the probe 40 to serve as a poration means for forming a micropore 30 in the tissue 5. Alternatively, the probe 40 can comprise a heated element for porating the biological membrane 10, such as the above-described heated probe comprising an electrically-heated probe or an optically-heated probe. In yet another alternate embodiment, the micropore 30 can be separately formed by other poration means, the probe 40 serving solely to deliver the flux enhancer 42 to the micropore 30.

The flux enhancer 42 can be carried in a tube 46 within the probe 40, or can be carried on the outer surface 48 of the probe. Transfer means is provided for transferring or releasing at least a portion of the flux enhancer 42 carried by the probe 40 into the tissue. For example, flux enhancer 42 can be injected into the tissue 5 from a tube 46 in the probe by a syringe or other pressurization means connected to the probe. Alternatively, heating of the probe 40 can serve to release the flux enhancer 42, such as by vaporization of a portion of the quantity of flux enhancer carried on the probe 40.

Figure 3:
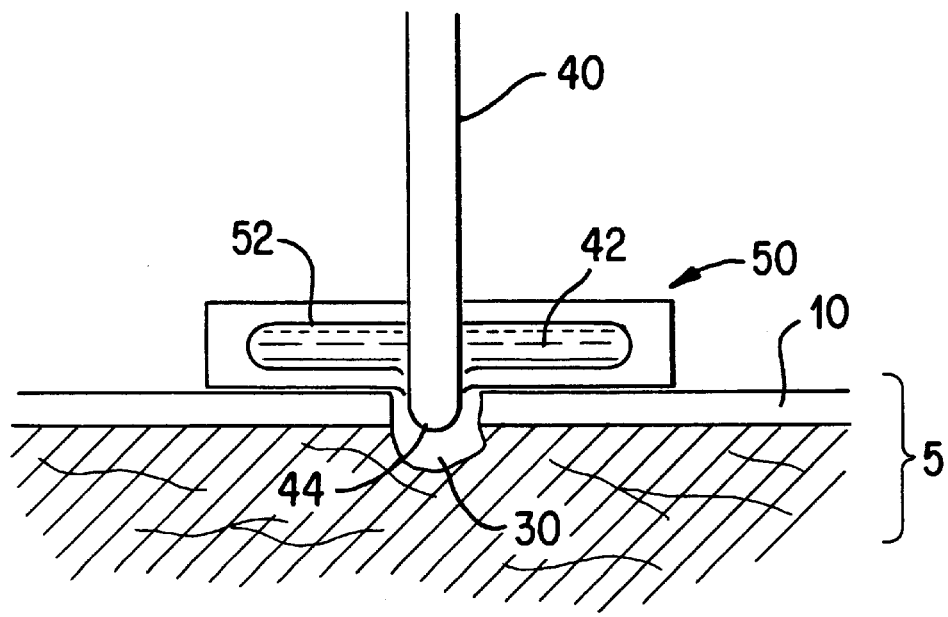
FIG. 3 is an enlarged diagram showing the delivery of a flux enhancer from a reservoir using a probe according to another embodiment of the present invention.

Another embodiment is shown in FIG. 3. A carrier device 50 comprises a reservoir 52 containing an effective amount of flux enhancer 42 for positioning on or adjacent to the surface of a biological membrane. The probe or penetration device 40 (described above) is inserted into and through the reservoir 52 to release the flux enhancer 42 and to form the micropore 30. The sharp tip 44 penetrates the carrier device 50 and the biological membrane 10. Alternatively, the probe 40 is a heated probe and forms the micropore by thermal ablation.

Preferably, sufficient energy is applied to the flux enhancer 42 to vaporize at least a portion of the flux enhancer. The vaporization of the flux enhancer 42 provides several advantages. For example, in its vapor state, a flux enhancer 42 such as ammonia more readily permeates into the tissue, thereby better enhancing the flux rate of fluids in the tissue 5. Vaporization of the flux enhancer 42 also allows the pressurized release of the flux enhancer into the micropore 30, which further enhances the flux rate of fluids in the tissue. A variety of methods and energy sources can be used to vaporize the flux enhancer 42, including: kinetic energy transfer, such as by application of ultrasound to the reservoir 52 of flux enhancer 42; electromagnetic radiation, such as microwave heating; conduction; or convection. Several examples are discussed in greater detail below.

For example, energy for the vaporization of the flux enhancer is provided by conduction, through the introduction of a probe 40, heated by the mechanisms above-described. The introduction of the heated probe 40 through the reservoir 52 of flux enhancer 42 and into the tissue 5, in a single step, advantageously porates the tissue 5 substantially simultaneously with the vaporization and delivery of the flux enhancer 42 to the tissue 5. Registration of the reservoir 52 of flux enhancer 42 on the tissue 5 over the site where the micropore is to be formed is maintained to ensure delivery into the micropore 30.

Figure 4:
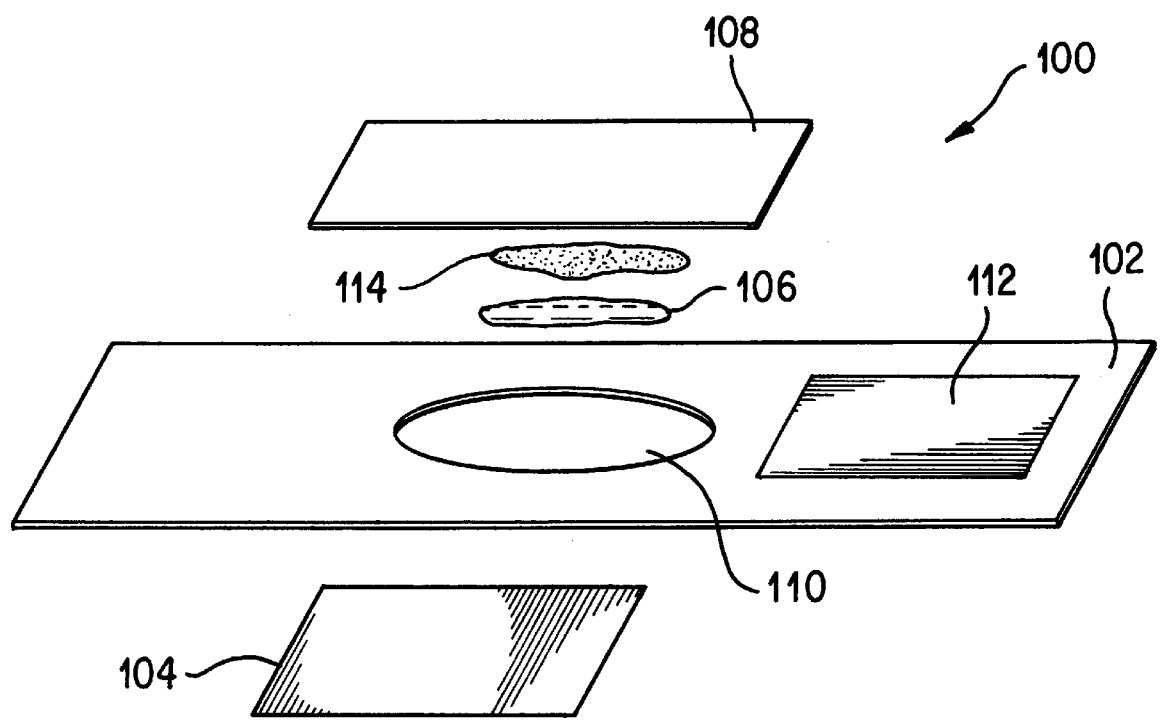
FIG. 4 is an exploded view showing a device for facilitating the poration of a biological membrane and the delivery of a flux enhancer according to the present invention.

Turning to FIG. 4, a carrier device according to another embodiment is generally shown at reference numeral 100. The carrier device 100 comprises a substrate layer 102, an energy absorbing layer 104, an effective amount of flux enhancer 106, and a cover layer 108 transparent to the electromagnetic energy. The substrate layer 102 supports the various components of the device, and defines an aperture 110 therein which is aligned with the energy absorbing layer 104 and the transparent cover layer 108. The energy absorbing layer 104 is positioned on a bottom surface of the substrate layer 102 whereby it can be placed in contact with the biological membrane. A reservoir or chamber is defined in the space of the aperture 110 between the energy absorbing layer 104 and the transparent cover layer 108. Thus, the reservoir is sealed in a sandwich-like structure between the energy absorbing layer 104 and the transparent cover layer 108. This reservoir contains the flux enhancer 106. A collecting element 112, such as an absorptive assay layer (well known in the art) is optionally also included on another portion of the substrate layer 102. The substrate layer 102 may include an adhesive on a bottom portion thereof for attachment to skin, for example. Other attachment means, such as surgical tape, etc., are also suitable.

A device for performing many functions in a microporation/harvesting/analysis procedure is disclosed in co-pending U.S. Provisional Application Ser. No. 60/077135, entitled "Integrated Poration, Harvesting and Analysis Device, and Method Therefor," filed on Mar. 6, 1998, the entirety of which is incorporated herein by reference.

The quantity of flux enhancer 106 can comprise a solid, gel, liquid, or vapor. It has been found that the use of a liquid flux enhancer reduces lateral heat transfer in the carrier device 100, thereby reducing any burning sensation observed by a person. Fusion means, such as a chemical binder or a carrier liquid or gel, can be provided for maintaining the quantity of flux enhancer 106 intact.

The substrate layer 102 is preferably made of biocompatible material, such as polycaprolactone or celluloseacetate which are commercially available.

The energy absorbing layer 104 is capable of absorbing energy received from an external source, such as a laser or other source of focused optical energy, converting that energy to heat, and transferring that heat to a target portion of the tissue to form at least one micropore by ablation. For example, the energy absorbing layer 104 comprises a dye layer, which can be formed of any energy absorbing material reactive with the external energy source, or of a nonabsorbing substrate having an absorbing material applied thereon. A plastic film carrier treated with copper phthalocyanine (CPC) dye has been found to provide acceptable energy absorption from a source of light at wavelengths between 750–950 nm. Other materials are known to absorb optical energy at specific ranges of wavelengths, and can be used with energy sources generating optical energy within those ranges. In this embodiment, it is preferable that the energy source not generate energy at wavelengths that are absorbed by the target biological tissue, so that the possibility of inadvertent injury to the tissue is minimized.

Figure 5:
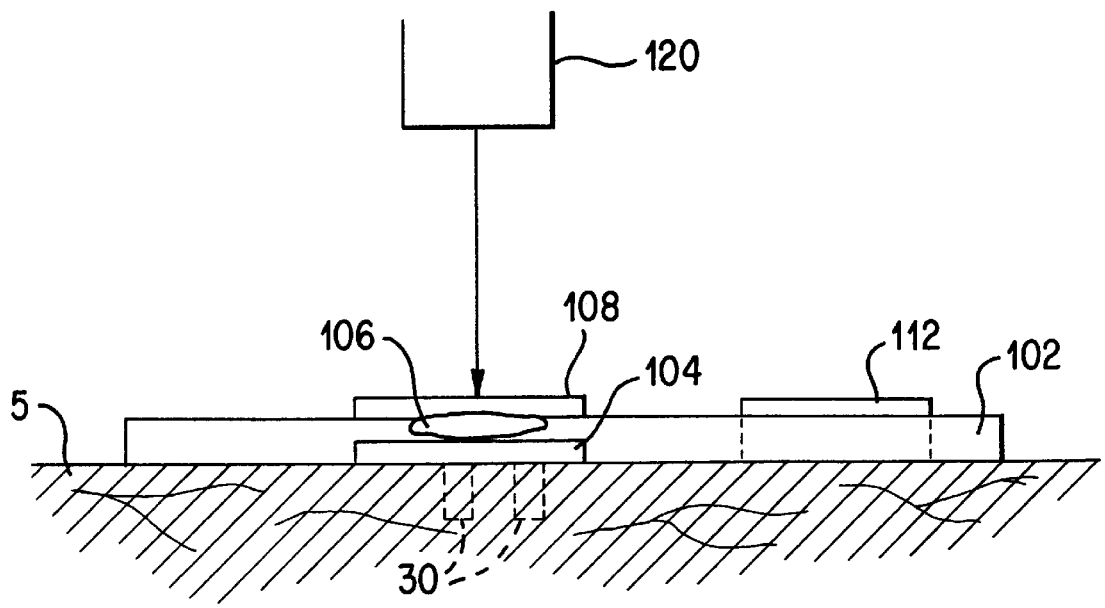
FIG. 5 is an enlarged view showing the delivery of a flux enhancer from the device shown in FIG. 4.

The use of the carrier device 100 is described in conjunction with FIG. 5. The carrier device 100 is positioned on the surface of a biological tissue to be porated, such as skin. A source of electromagnetic energy 120, such as optical energy, is focused at the transparent cover layer 108 on the carrier device 100. The focused optical energy is absorbed by the energy absorbing layer 104 thereby heating it. Heat generated by absorption of the focused optical energy is transferred to the flux enhancer 106 to heat it ultimately to a temperature to vaporize at least a portion of it. Substantially simultaneously therewith, heat generated by absorption of the focused optical energy is transferred to the tissue 5 beneath the energy absorbing layer 104 to ablate one or more micropores 30 in the tissue. The heat generated by the absorption of the focused optical energy eventually destroys a portion of the energy absorbing layer 104, melting or burning an opening therethrough, allowing the release of at least a portion of the flux enhancer 106 (now vaporized) into the tissue 5 through the micropore 30.

The carrier device 100 initially comprises an intact energy absorbing layer, which is normally impermeable to the flux enhancer 106, but which is made to rupture so as to release the flux enhancer 106 upon absorption of sufficient energy from the external energy source. By simultaneously ablating the tissue with optical energy and vaporizing the flux enhancer through one carrier device, there is inherently provided registration with the formed micropores to ensure delivery of the vaporized flux enhancer into the micropores.

For collection applications, the carrier device 100 is placed over the porated site so that the collecting element 112 is in position to collect fluid, such as interstitial fluid. Additionally, suction may be applied directly over the site before, during or after the micropores are formed and the flux enhancer is released. Such suction devices are well known in the art.

Figure 7:
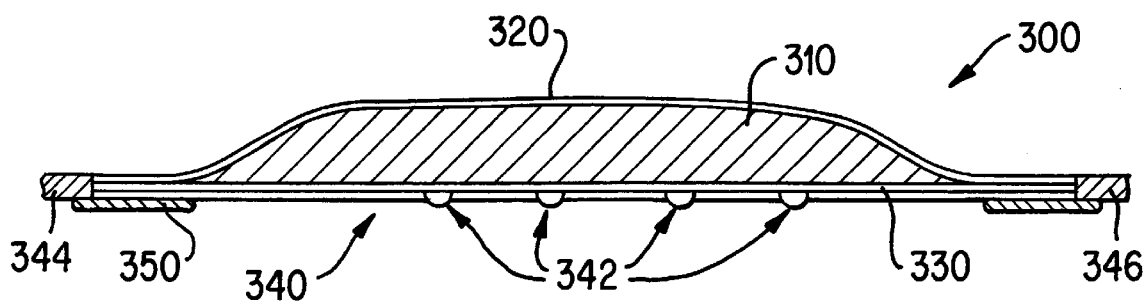
FIG. 7 is side view of a device suitable for microporating tissue and delivering a drug into the microporated tissue.
Figure 8:
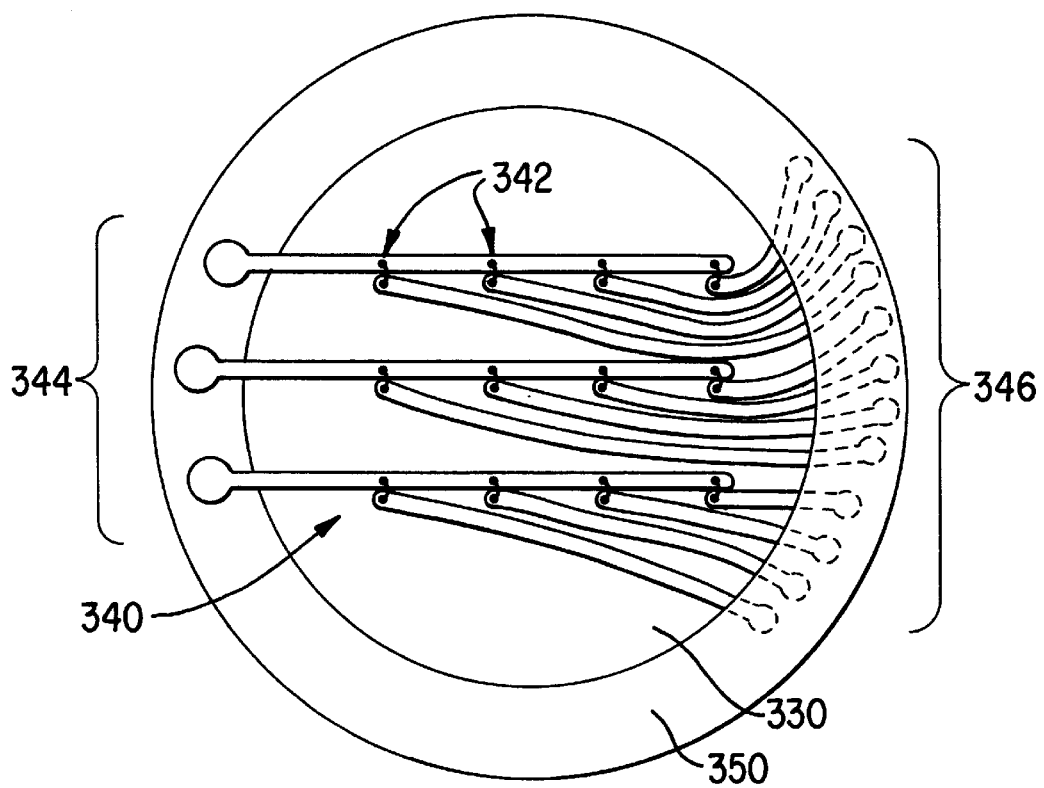
FIG. 8 is a bottom view of the device of FIG. 7.
Figure 9:
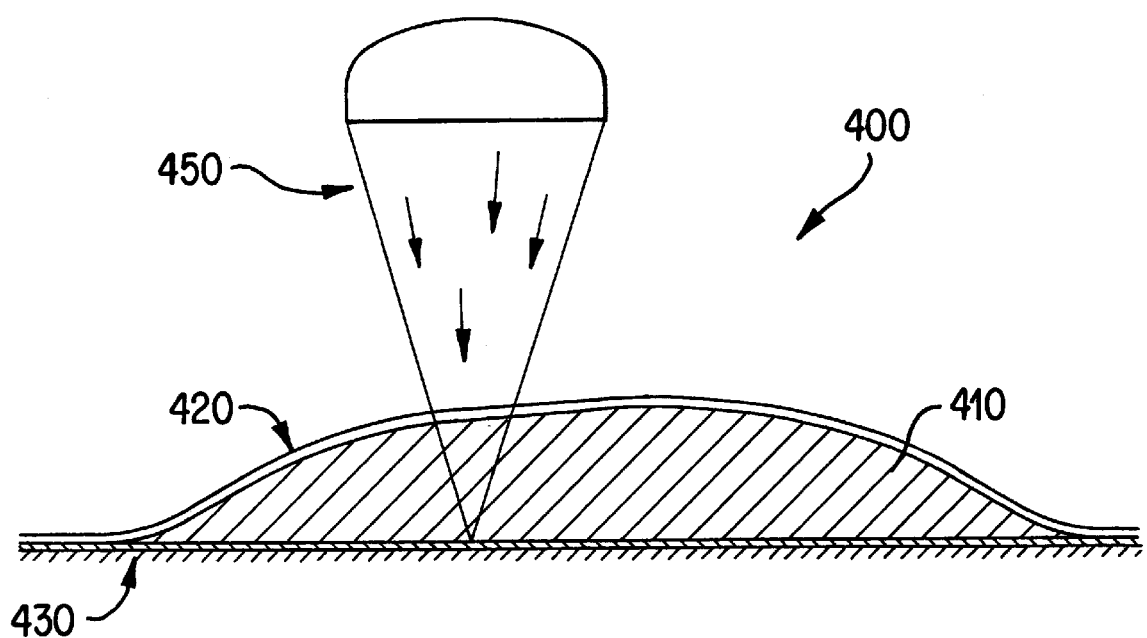
FIG. 9 is a side view of another device suitable for microporating tissue and delivering a drug into the microporated tissue.

For drug delivery applications, the carrier device 100 further comprises a quantity of a drug 114 for deliver into the tissue. The drug can be in solid, gel, liquid or vapor form. The quantity of drug 114 can be contained in the reservoir of the carrier device 100 as described above, together with the flux enhancer 106. FIGS. 7–9 illustrate devices which are suitable for delivery flux enhancer during microporation and delivery of a drug into microporated tissue.

Figure 6:
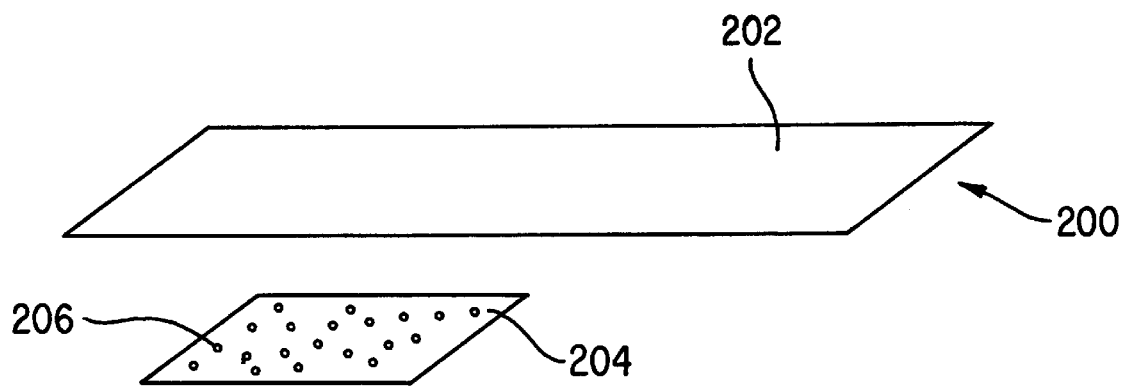
FIG. 6 is an exploded view showing another device for facilitating the poration of a biological membrane and the delivery of a flux enhancer according to the present invention.

Another embodiment of a carrier device is shown in FIG. 6. The carrier device 200 comprises a transparent substrate layer 202 and an energy absorbing layer 204 on a bottom surface thereof. The energy absorbing layer 204 is treated with or otherwise incorporates a quantity of flux enhancer 206. The flux enhancer 206 may be in granular or powdered form and is applied to or incorporated in the energy absorbing layer 204. The energy absorbing layer 204 may comprise a structure similar to the photosensitizing assembly described in the co-pending U.S. Provisional Application Ser. No. 60/077135, entitled "Integrated Poration, Harvesting and Analysis Device, and Method Therefor." For example, ammonia bi-carbonate crystals are suspended in the energy absorbing layer 204 based on the fabrication techniques described in the aforementioned co-pending application. An adhesive may be provided on the bottom surface of the substrate layer 202 to attach the device to a site. The device 200 is used in the same manner as device 100 shown in FIG. 5. As described above, the energy absorbing layer 204 absorbs energy from an external energy source, thereby heating it. Heat is transferred to the underlying tissue to ablate a portion of the tissue and to form one or more micropores. In addition, the heat in the energy absorbing layer vaporizes the flux enhancer incorporated therein, thereby releasing it into the micropore(s). The energy absorbing layer 204 could also be treated with a quantity of a drug that would be suitably released by heat vaporization.

The delivery of flux enhancer into the target biological tissue through a micropore increases the rate at which fluids will flow through the tissue. Poration of the tissue to a selected depth allows the delivery of flux enhancer to a selected tissue or a selected portion of a tissue. The present invention thereby provides significantly improved results, as compared to previously known collection and delivery methods.

Turning to FIGS. 7 and 8, a device for containing a drug to be delivered to microporated tissue and for delivery a flux enhancer, is shown generally at reference numeral 300. The device 300 is a reservoir patch containing a quantity of a drug mixture 310 in gaseous, liquid gel or solid form. The reservoir is defined and contained between a upper membrane 320 which is sealed to a lower membrane 330. On the bottom surface of the lower membrane 330 a printed circuit 340 is disposed, preferably in a central region of the lower membrane 330. At selected points in the printed circuit 340 a plurality of electrically heated probes 342 are connected and attached. More specifically, the electrically heated probes 342 are connected between two sets of electrically conductive contact pads 344 and 346. The electrically heated probes 342 are similar to the heated wires described in the foregoing, and in the co-pending applications. Furthermore, around a periphery of the lower membrane 330, adhesive may be provided to hold the device 300 onto the tissue. The entire lower membrane 300 may be sealed by pealable cover that keeps the device sterile and protecting the circuit 340 from exposure. Thus, the device 300 may be completely disposable. A quantity of flux enhancer may be applied to the surface of the electrically heated probes 342 by coating the probes with a mixture containing one of the flux enhancers described in the foregoing.

In operation, the device 300 is installed on the surface of the tissue or biological membrane. The adhesive cover is removed and the device is firmly attached. Electrical current is supplied to the circuit 340, energizing the electrically heated probes 342. The probes 342 will heat up and thermally ablate the tissue forming the micropores therein. In addition, the flux enhancer mixture on the surface of the electrically heated probes vaporizes and is taken up into the tissue through the micropores. Substantially simultaneous with the thermal creation of the micropores, the lower membrane 330 will melt and multiple channels will be formed for delivering the drug mixture 310 into the micropores created in the tissue.

Once the micropores have been formed, the electrically heated probes 342 can be connected to a source of very mild electrical voltage to electroporate the tissue. This is further described in co-pending U.S. application Ser. No. 09/036, 169, entitled "Apparatus And Method For Electroporation Of Microporated Tissue For Enhancing Flux Rates For Monitoring And Delivery Applications," filed on Mar. 6, 1998 date, now U.S. Pat. No. 6,022,316 the entirety of which is incorporated herein by reference. See also International Application No. PCT/US97/24127, entitled "Microporation of Biological Tissue For Delivery of Bio-Active Agents," filed Dec. 30, 1997, the entirety of which is incorporated herein by reference. An AC or DC current can be created across the micropores to induce an active ion-pumping of the drug into the tissue. This could be further enhanced by providing two separate reservoirs with complementary charged solutions in each to support a DC ion flow which would yield a net positive flux of the drug into the tissue.

Another technique to control the flux rate is to use the electrically heated probes, or separate heated probes built into the device, to heat up the drug mixture, causing subsequent thermal expansion and an increase in the pressure within the reservoir. This heating process could be extended to the point where some portion of the drug mixture is vaporized. This would generate a large increase in the pressure inside the reservoir, which would remain high until the vapor subsequently condensed and the pressure is returned to an initial passive state. Still another technique is to contact the electrically heated probes with the drug mixture and use them as electrodes by developing a potential between them as a means to electrolyze some elements of the solution to liberate a gas from the liquid or gel mixture, causing the desired increase in pressure.

Turning to FIG. 9, another device, shown generally at reference numeral 400 is provided to delivery flux enhancer to microporated tissue and to delivery a drug into the tissue. The device 400 is a reservoir patch device that contains a reservoir of a drug mixture 410, similar to that described in conjunction with FIGS. 7 and 8. The drug mixture 410 is contained within a chamber defined by an upper membrane 420 and a lower membrane 430. The lower membrane 430 is formed of a non-porous plastic material which has been treated with an energy absorbing compound similar to that described in conjunction with FIG. 6. In addition, a quantity of flux enhancer is suspended within the energy absorbing compound of the lower membrane 430. The upper membrane 420 is formed of optically transparent material to allow the passage of optical energy therethrough. The drug mixture 410 is likewise transparent to optical energy.

The operation of the device 400 is similar to that described in conjunction with FIG. 6. That is, the device is applied to the tissue and a beam of optical energy, shown at reference numeral 450 is focused onto device through the upper membrane 420 onto the lower membrane 430. The lower membrane 430 responds to the optically energy to heat up and form micropores therein, and also melts at focused spots of the optical energy, thus permitting the drug mixture 410 to be released into the tissue through the micropores. The lower membrane 430 could be further treated with an adhesive around its entire surface, or its peripheral edges, or can be treated with a compound designed to reduce the thermal impedance between the heated spots and the tissue surface. Alternatively, the device 400 may comprise two chambers or reservoirs, one for the flux enhancer and one for the drug.

Preferably, the devices described herein are constructed such that the entire drug reservoir, poration elements, and optionally controlling circuitry and power source can be contained in a cone-time-use package approximately the size of a pocket watch or smaller. This platform is suitable for applications such as post-operative delivery of pain killers or other acute treatment regimens for which a controllable transdermal delivery system would be useful.

In drug delivery applications, the delivery of a flux enhancer to the biological tissue allows increased rates of drug introduction into target tissue or into the bloodstream. Thus, a given quantity of a drug can be delivered to a tissue or into the bloodstream in a shorter period of time, as compared with previously known delivery methods. Also, by the selective control of the depth of poration and of the delivery of flux enhancer, the present invention permits effective delivery of a drug to deeper tissue or tissue more remote from the site of application than could be achieved using previous non-invasive or minimally invasive delivery techniques. For example, the present invention enables delivery of a drug to the capillary depth of a tissue, thereby providing improved uptake into the bloodstream before the drug is metabolized by the reaction of the body to a foreign substance. This is accomplished by porating the tissue to a selected depth whereby the flux enhancer can be delivered to the walls of the capillaries or to tissue adjacent the capillaries, and delivering the flux enhancer and the drug through the micropore. Iontophoresis, sonic energy, mechanical pressure and manipulation or other motive forces can be used to further enhance the rate of drug delivery. Delivery of the flux enhancer and the drug in this manner results in faster uptake of the drug into the bloodstream. Thus, the rate of uptake of a drug by the subject organism can be controlled as desired by appropriate selection of the depth of poration and application of the flux enhancer and control of the other motive forces described herein.

The above-described embodiments are given as illustrative examples only, and are not intended to be limiting or exhaustive. It will be readily apparent to those of ordinary skill in the art that many additions, deletions and modifications may be made without departing from the spirit and scope of the present invention, as defined by the claims below.

What is claimed is:

1. A method for enhancing the flux rate of a substance through a porated tissue, comprising the step of delivering an effective amount of a flux enhancer into the tissue through at least one micropore made into an outer layer of the tissue so that the flux enhancer acts on tissue structures in or beneath the outer layer thereby increasing the flux rate of a substance through the tissue, wherein the step of delivering the flux enhancer comprises step of positioning a quantity of flux enhancer adjacent the porated tissue and applying sufficient energy to the quantity of flux enhancer to vaporize at least a portion of the quantity of flux enhancer, thereby releasing at least a portion of the quantity of flux enhancer into the tissue through the at least one micropore.

2. The method of claim 1, wherein the step of delivering the flux enhancer comprises inserting a probe carrying the effective amount of flux enhancer into the tissue.

3. The method of claim 1, wherein the step of applying sufficient energy to the quantity of flux enhancer comprises introducing a heated element into the quantity of flux enhancer.

4. The method of claim 1, wherein the step of positioning a quantity of the flux enhancer at the site comprises placing a carrier device having a reservoir containing the quantity of flux enhancer adjacent the porated tissue, and wherein the step of applying sufficient energy comprises applying energy to the carrier device to vaporize at least a portion of the quantity of flux enhancer.

5. The method of claim 4, and further comprising delivering a drug contained in the reservoir through the at least one micropore.

6. The method of claim 1, and further comprising delivering a quantity of a drug through the at least one micropore.

7. The method of claim 1, and further comprising collecting a sample of an analyte through the at least one micropore.

8. A method for enhancing the flux rate of a substance through a porated tissue, comprising the step of delivering an effective amount of a flux enhancer into the tissue through at least one micropore made into an outer layer of the tissue so that the flux enhancer acts on tissue structures in or beneath the outer layer thereby increasing the flux rate of a substance through the tissue, wherein the flux enhancer contains ammonia.

9. The method of claim 8, wherein the step of delivering the flux enhancer comprises inserting a probe carrying the effective amount of flux enhancer into the tissue.

10. The method of claim 8, wherein the step of delivering the flux enhancer comprises positioning a quantity of flux enhancer adjacent the porated tissue and releasing at least a portion of the quantity of flux enhancer into the tissue through the at least on micropore.

11. The method of claim 10, and further comprising the step of applying sufficient energy to the quantity of flux enhancer to vaporize at least a portion of the quantity of flux enhancer.

12. The method of claim 10, wherein the step of applying energy to the quantity of flux enhancer comprises introducing a heated element into the quantity of flux enhancer.

13. The method of claim 10, wherein the step of positioning a quantity of the flux enhancer at the site comprises placing a carrier device having a reservoir containing the quantity of flux enhancer adjacent the porated tissue, and wherein the step of releasing at least a portion of the quantity of flux enhancer into the tissue through the at least one micropore comprises applying energy onto the carrier device to vaporize at least a portion of the quantity of flux enhancer.

14. The method of claim 13, and further comprising the step of delivering a drug contained in the reservoir through the at least one micropore.

15. The method of claim 8, and further comprising delivering a drug into the tissue through the at least one micropore.

16. The method of claim 8, and further comprising collecting a sample of an analyte through the at least one micropore.

17. A method of enhancing the flux rate of a substance through a biological membrane, comprising steps of:
 (a) porating the biological membrane to form at least one micropore in the biological membrane; and
 (b) delivering an effective amount of a flux enhancer to through the micropore in the biological membrane, wherein the flux enhancer contains ammonia.

18. The method of claim 17, and further comprising the step of introducing a drug through the at least one micropore.

19. The method of claim 17, wherein the steps of porating and delivering comprise applying a sufficient amount of electromagnetic energy onto an energy absorbing layer placed adjacent the surface of the biological membrane, wherein the energy absorbing layer is treated with said effective amount of flux enhancer such that said reservoir is incorporated in said energy absorbing layer.

20. The method of claim 17, wherein the micropore extends to a selected depth into or through the biological membrane.

21. The method of claim 17, wherein the steps of porating and delivering comprise inserting a probe carrying a quantity of flux enhancer into the biological membrane.

22. The method of claim 21, wherein the step of inserting a probe comprises inserting a heated probe into the biological membrane.

23. The method of claim 17, wherein the step of delivering an effective amount of a flux enhancer comprises the steps of positioning a reservoir containing a quantity of flux enhancer adjacent the surface of the biological membrane, and releasing at least a portion of the quantity of flux enhancer from the reservoir into the at least one micropore.

24. The method of claim 23, and further comprising the step of applying sufficient energy to the reservoir of flux enhancer to vaporize at least a portion of the quantity of flux enhancer.

25. The method of claim 24, wherein the steps of porating the biological membrane and releasing at least a portion of the flux enhancer comprise the step of applying a sufficient amount of eletromagnetic energy onto an energy absorbing portion adjacent the reservoir to heat the energy absorbing portion to a temperature sufficient to form the at least one micropore and to vaporize at least a portion of the reservoir of flux enhancer.

26. The method of claim 25, wherein the step of measuring an impedance comprises measuring a complex impedance between the electrically heated probe and the electrode.

27. The method of claim 24, wherein the steps of porating the membrane and releasing at least a portion of the flux enhancer comprise the step of introducing a heated element through the reservoir and into the membrane.

28. The method of claim 23, and further comprising delivering a drug contained in the reservoir through the at least one micropore.

29. The method of claim 17, and further comprising the step of applying ultrasonic energy to the tissue to draw an interstitial fluid containing the analyte outwardly through the at least one micropore.

30. The method of claim 17, and further comprising the step of applying suction to the tissue to draw interstitial fluid comprising the analyte outwardly through the at least one micropore.

31. The method of claim 17, wherein the step of porating comprises measuring an impedance between an electrically heated probe that creates the micropore and an electrode spaced therefrom to control a depth of the micropore based on the impedance.

32. The method of claim 17, and further comprising collecting a sample of an analyte through the at least one micropore.

33. A method of enhancing the flux rate of a substance through a biological membrane, comprising steps of:
   (a) porating the biological membrane to form at least one micropore in the biological membrane;
   (b) delivering an effective amount of a flux enhancer to through the micropore in the biological membrane, wherein the step of delivering an effective amount of a flux enhancer comprises steps of positioning a reservoir containing a quantity of flux enhancer adjacent the surface of the biological membrane, and applying sufficient energy to the reservoir of flux enhancer to vaporize at least a portion of the quantity of flux enhancer thereby releasing at least a portion of the quantity of flux enhancer from the reservoir into the at least one micropore;

wherein the steps of porating the membrane and applying sufficient energy comprise the step of introducing a heated element through the reservoir and into the biological membrane.

34. The method of claim 33, wherein the micropore extends to a selected depth into or through the biological membrane.

35. The method of claim 33, and further comprising the step of applying ultrasonic energy to the tissue to draw an interstitial fluid containing the analyte outwardly through the at least one micropore.

36. The method of claim 33, and further comprising the step of applying suction to the tissue to draw interstitial fluid comprising the analyte outwardly through the at least one micropore.

37. The method of claim 33, wherein the step of porating comprises measuring an impedance between an electrically heated probe that creates the micropore and an electrode spaced therefrom to control a depth of the micropore based on the impedance.

38. The method of claim 37, wherein the step of measuring an impedance comprises measuring a complex impedance between the electrically heated probe and the electrode.

39. The method of claim 33, and further comprising the step of introducing a drug through the at least one micropore.

40. The method of claim 33, and further comprising collecting a sample of an analyte through the at least one micropore.

* * * * *

UNITED STATES PATENT AND TRADEMARK OFFICE
CERTIFICATE OF CORRECTION

PATENT NO. : 6,173,202 B1
DATED : January 9, 2001
INVENTOR(S) : JONATHAN A. EPPSTEIN It is certified that error appears in the above-identified patent and that said Letters Patent is hereby corrected as shown below:

On the cover page, under the caption "Other Publications", line 15, change "Solutionin" to --Solution in--

In Column 4, line 55, change "ammonia heparin," to --ammonium heparin,-- change "ammonia bicarbonate;" to --ammonium bicarbonate;--

Signed and Sealed this

Twenty-ninth Day of May, 2001

Attest:

NICHOLAS P. GODICI

Attesting Officer

Acting Director of the United States Patent and Trademark Office